United States Patent
Iwai

(10) Patent No.: US 8,921,613 B2
(45) Date of Patent: Dec. 30, 2014

(54) POLYNUCLEAR POLY(PHENOL) FAMILY

(75) Inventor: Tatsuya Iwai, Wakyama (JP)

(73) Assignee: Honshu Chemical Industry Co., Ltd., Tokyo (JP)

( * ) Notice: Subject to any disclaimer, the term of this patent is extended or adjusted under 35 U.S.C. 154(b) by 410 days.

(21) Appl. No.: 13/516,172

(22) PCT Filed: Dec. 15, 2010

(86) PCT No.: PCT/JP2010/072526
§ 371 (c)(1),
(2), (4) Date: Jul. 6, 2012

(87) PCT Pub. No.: WO2011/074597
PCT Pub. Date: Jun. 23, 2011

(65) Prior Publication Data
US 2012/0277479 A1  Nov. 1, 2012

(30) Foreign Application Priority Data
Dec. 15, 2009  (JP) .................. 2009-284007

(51) Int. Cl.
*C07C 39/17*  (2006.01)

(52) U.S. Cl.
CPC .............. *C07C 39/17* (2013.01); *C07C 2101/14* (2013.01)
USPC .......................................... 568/721; 568/720

(58) Field of Classification Search
CPC ...... C07C 39/17; C07C 39/16; C07C 101/16; C07C 2101/14
USPC ................................. 568/721, 720
See application file for complete search history.

(56) References Cited

U.S. PATENT DOCUMENTS

| | | | | |
|---|---|---|---|---|
| 5,304,624 A | * | 4/1994 | Koike et al. | 528/98 |
| 5,554,797 A | * | 9/1996 | Schulz et al. | 568/592 |
| 2007/0232839 A1 | | 10/2007 | Yoshitomo et al. | |

FOREIGN PATENT DOCUMENTS

| | | |
|---|---|---|
| JP | 07-69954 A | 3/1995 |
| JP | 07-258142 A | 10/1995 |
| JP | 11-199533 A | 7/1999 |
| JP | 2001-199920 A | 7/2001 |
| JP | 2007-142353 A | 6/2007 |
| JP | 2007-326847 A | 12/2007 |
| JP | 2008-083124 * | 4/2008 |
| JP | 2008-230984 A | 10/2008 |
| JP | 2009-069450 A | 4/2009 |

OTHER PUBLICATIONS

International Search Report mailed by Japan Patent Office on Feb. 22, 2011 in the corresponding PCT patent application No. PCT/JP2010/072526.

* cited by examiner

*Primary Examiner* — Rosalynd Keys
(74) *Attorney, Agent, or Firm* — Knobbe, Martens, Olson & Bear LLP

(57) ABSTRACT

Provided is a polynuclear poly(phenol)family represented by general formula (1). In general formula (1), $R_1$s are each independently $C_{1-8}$ alkyl group, $C_{1-8}$ alkoxy group, an aromatic hydrocarbon group, or a $C_{1-8}$ saturated hydrocarbon group having an aromatic hydrocarbon group; n is 0 or an integer of 1 to 3; X is a hydroxyphenyl group represented by general formula (2); and A is a tetravalent carbon atom group or a tetravalent saturated hydrocarbon group having two or more carbon atoms, with the proviso that when A is a tetravalent saturated hydrocarbon group having two or more carbon atoms, two carbon atoms in the A group are each bonded to two phenyl groups.

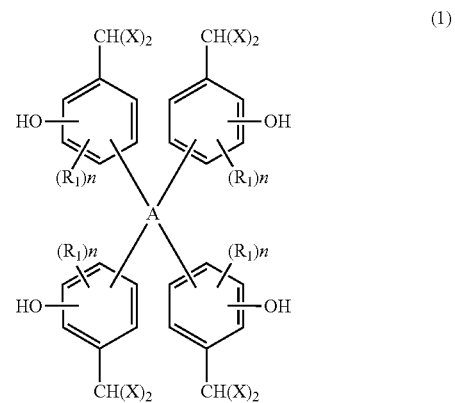

(1)

2 Claims, No Drawings

POLYNUCLEAR POLY(PHENOL) FAMILY

TECHNICAL FIELD

The present invention relates to a novel polynuclear poly (phenol) family, and more specifically to a polynuclear poly (phenol) family constituted by a tetrakis(methine-substituted hydroxyphenyl) frame having four terminal phenyl groups in the molecule and where the phenyl nucleus has methine groups and hydroxyl groups as nuclear substitution groups, wherein each methine group in the frame is further substituted with two hydroxyphenyl groups.

PRIOR ART

There have been calls in recent years for further improvement of materials such as epoxy resin, photosensitive resist and the like for electronic components with the emergence of fine processing technologies, etc., and novel material compounds are required to meet such demand. As examples of such compounds, polynuclear polyphenol compounds such as 1-[α-methyl-α-{3-bis(2,5-dimethyl-4-hydroxyphenyl) methyl-5-methyl-4-hydroxyphenyl}ethyl]-4-[α,α-bis{3-bis (2,5-dimethyl-4-hydroxyphenyl)methyl-5-methyl-4-hydroxyphenyl}ethyl]benzene (Patent Literature 1) and bis [3-{3-bis(2,5-dimethyl-4-hydroxyphenyl)methyl-4-carboxymethoxyphenyl}methyl-2,5-dimethyl-4-carboxymethoxyphenyl]methane (Patent Literature 2) and the like have been heretofore known. However, these traditionally known polynuclear polyphenol compounds do not provide enough functions such as heat resistance and resolution and the like when used as raw materials for resist material, and therefore raw material compounds for resist material offering higher heat resistance and higher resolution are being required.

PRIOR ART LITERATURES

Patent Literatures

Patent Literature 1: International Patent Application Publication No. 2007/142353
Patent Literature 2: International Patent Application Publication No. 2009/069450

SUMMARY OF THE INVENTION

Problems to be Solved by the Invention

The present invention was developed in light of the aforementioned situation pertaining to traditional polynuclear poly(phenol) compounds and the object of the present invention is to provide a novel polynuclear poly(phenol) compound offering high heat resistance.

Means for Solving the Problems

According to the present invention, a polynuclear poly (phenol) family expressed by general formula (1) below is provided:

[Chemical 1]

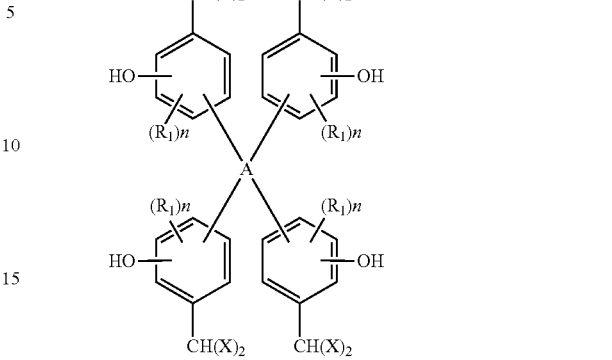

General Formula (1)

(In the formula, $R_1$s are each independently an alkyl group with 1 to 8 carbon atoms, alkoxyl group with 1 to 8 carbon atoms, aromatic hydrocarbon group, or saturated hydrocarbon group with 1 to 8 carbon atoms and having an aromatic hydrocarbon group; n is 0 or an integer of 1 to 3; X is a hydroxyphenyl group expressed by general formula (2) below; and A is a tetravalent carbon atom group or tetravalent saturated hydrocarbon group with 2 or more carbon atoms; wherein when A is a tetravalent saturated hydrocarbon group with 2 or more carbon atoms, two carbon atoms in the A group are each bonded to two phenyl groups.)

[Chemical 2]

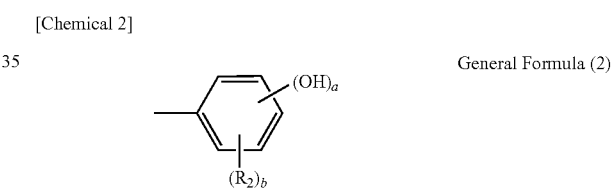

General Formula (2)

(In the formula, $R_2$ is an alkyl group with 1 to 8 carbon atoms, alkoxyl group with 1 to 8 carbon atoms, aromatic hydrocarbon group, or saturated hydrocarbon group with 1 to 8 carbon atoms and having an aromatic hydrocarbon group; a is an integer of 1 to 3; and b is 0 or an integer of 1 to 4; wherein when $1 \leq a+b \leq 5$ and b is 2 or greater, $R_2$s may be either the same or different.)

In addition, a polynuclear poly(phenol) family where general formula (2) above is expressed by general formula (3) below is a desired embodiment of the present invention:

[Chemical 3]

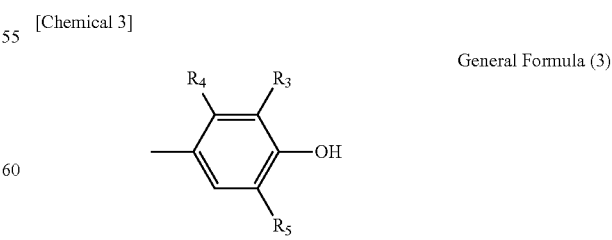

General Formula (3)

(In the formula, $R_3$, $R_4$ and $R_5$ are each independently a hydrogen atom, alkyl group with 1 to 8 carbon atoms, alkoxyl group with 1 to 8 carbon atoms, aromatic hydrocarbon group, or saturated hydrocarbon group with 1 to 8 carbon atoms and having an aromatic hydrocarbon group.)

Effects of the Invention

A polynuclear poly(phenol) family according to the present invention is a polynuclear poly(phenol) compound having a central frame which is a tetrakis(methine group-substituted hydroxyphenyl) where the same carbon atom is bonded to four phenyl groups having methine groups and hydroxyl groups, or two different carbon atoms are each bonded to two phenyl groups having methine groups and hydroxyl groups, in the saturated hydrocarbon group, wherein each methine group is bonded further to two hydroxyphenyl groups, and four triphenylmethane frames are present in the molecule, which results in excellent heat resistance represented by higher glass transition temperature, etc. In addition, excellent alkali dissolution speed is expected because the molecule has 12 phenolic hydroxyl groups. Accordingly, when a compound according to the present application for patent is used as photosensitive resist material, particularly as resist material for electron beam or EUV or its raw material, by, for example, substituting the hydroxyl group with an acid dissociation group, excellent effects such as improvement of heat resistance and resolution of resist can be expected.

Furthermore, when it is used as material polyphenol compound for phenol resin, epoxy resin, etc., improvement of heat resistance (high glass transition temperature), flexibility and water resistance can be expected.

MODE FOR CARRYING OUT THE INVENTION

A novel polynuclear poly(phenol) family according to the present invention is expressed by general formula (1) below:

[Chemical 1]

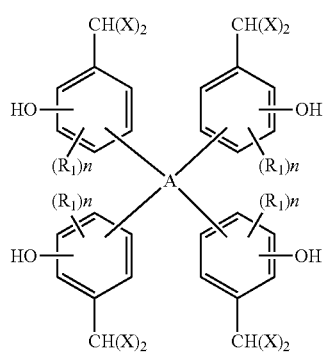

General Formula (1)

(In the formula, $R_1$s are each independently an alkyl group with 1 to 8 carbon atoms, alkoxyl group with 1 to 8 carbon atoms, aromatic hydrocarbon group, or saturated hydrocarbon group with 1 to 8 carbon atoms and having an aromatic hydrocarbon group; n is 0 or an integer of 1 to 3; X is a hydroxyphenyl group expressed by general formula (2) below; and A is a tetravalent carbon atom group or tetravalent saturated hydrocarbon group with 2 or more carbon atoms; wherein when A is a tetravalent saturated hydrocarbon group with 2 or more carbon atoms, two carbon atoms in the A group are each bonded to two phenyl groups.)

[Chemical 2]

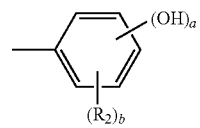

General Formula (2)

(In the formula, $R_2$ is an alkyl group with 1 to 8 carbon atoms, alkoxyl group with 1 to 8 carbon atoms, aromatic hydrocarbon group, or saturated hydrocarbon group with 1 to 8 carbon atoms and having an aromatic hydrocarbon group; a is an integer of 1 to 3; and b is 0 or an integer of 1 to 4; wherein when $1 \leq a+b \leq 5$ and b is 2 or greater, $R_2$s may be either the same or different.)

In addition, a polynuclear poly(phenol) family where general formula (2) above is expressed by general formula (3) below is a desired embodiment of the present invention:

[Chemical 3]

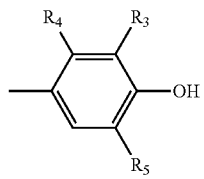

General Formula (3)

(In the formula, $R_3$, $R_4$ and $R_5$ are each independently a hydrogen atom, alkyl group with 1 to 8 carbon atoms, alkoxyl group with 1 to 8 carbon atoms, aromatic hydrocarbon group, or saturated hydrocarbon group with 1 to 8 carbon atoms and having an aromatic hydrocarbon group.)

In general formula (1) above, the bonding position of the hydroxyl group to the benzene ring is preferably the o-position and/or p-position, or more preferably the p-position, relative to the bonding position of A to the benzene ring.

Also in general formula (1), in the formula, specific examples of the alkyl group with 1 to 8 carbon atoms, being represented by $R_1$, include straight-chain, branched-chain or cyclic alkyl group such as methyl group, ethyl group, propyl group, butyl group, t-butyl group, pentyl group, 3-methylpentyl group, cyclopropyl group, cyclopentyl group, 3-methylcyclopentyl group, cyclohexyl group, 2,4-dimethyl cyclohexyl group, cycloheptyl group or the like. Additionally, specific examples of the alkoxyl group with 1 to 8 carbon atoms include straight-chain, branched-chain or cyclic alkoxyl group such as methoxy group, ethoxy group, propoxy group, isopropoxy group, butoxy group, t-butoxy group, pentyloxy group, isopentyloxy group, cyclopropoxy group, cyclopentyloxy group, 3-methylcyclopentyloxy group, cyclohexyloxy group, 2,4-dimethylcyclohexyloxy group, cycloheptyloxy group or the like. Among the above, a straight-chain or branched-chain alkyl group or alkoxyl group, with 1 to 4 carbon atoms, or cyclic alkyl group or cyclic alkoxyl group with 5 to 8 carbon atoms is preferred, of which a straight-chain or branched-chain alkyl group with 1 to 4 carbon atoms is particularly preferred. Furthermore, n is preferably 1.

Also with the aromatic hydrocarbon group or saturated hydrocarbon group with 1 to 8 carbon atoms and having an aromatic hydrocarbon group, being represented by $R_1$, the aromatic hydrocarbon group may or may not be substituted with the alkyl group and/or alkoxyl groups such as methyl group, methoxy group or the like, and specific examples include the phenyl group, 4-methylphenyl group, etc., where the total number of carbon atoms of the substituted alkyl group is preferably 1 to 4.

The saturated hydrocarbon group with 1 to 8 carbon atoms and having an aromatic hydrocarbon group has its aromatic hydrocarbon group substituted with the side chain or main chain of an alkyl group with 1 to 8 carbon atoms, and specific examples include the benzyl group, 1-phenylethyl group, and (4-methylphenyl) methyl group. Also to facilitate industrial application, preferably $R_1$ is substituted at at least one of the o-position and p-position of the hydroxyl group. In particular, preferably n is 1 and the methine group and $R_1$ are each substituted at the o-position of the hydroxyl group, respectively.

Also in general formula (1), A is a tetravalent carbon atom group or tetravalent saturated hydrocarbon group with 2 or more carbon atoms; wherein, when A is a tetravalent saturated hydrocarbon group with 2 or more carbon atoms, two carbon atoms in the A group are each bonded to two phenyl groups. Here, the tetravalent saturated hydrocarbon group is one with 2 to 50 carbon atoms, or preferably one with 2 to 30 carbon atoms, where specific examples include, for example, a straight-chain or branched-chain saturated hydrocarbon group, single-ring alicyclic saturated hydrocarbon group, multi-ring alicyclic saturated hydrocarbon group, bridged-ring alicyclic saturated hydrocarbon group or terpene saturated hydrocarbon, saturated hydrocarbon group containing both of these chain and cyclic ones, etc., all of which may have a substitution group. Specific, preferred examples of the tetravalent carbon atom group or tetravalent saturated hydrocarbon group with 2 or more carbon atoms include, for example, the following, among others:

[Chemical 4]

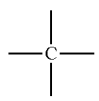

Formula

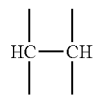

Formula

[Chemical 5]

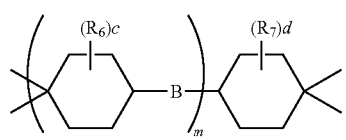

General Formula (4)

(In the formula, $R_6$ and $R_7$ are each independently an alkyl group with 1 to 8 carbon atoms; c and d are each independently 0 or an integer of 1 to 4; B is a single bond or bivalent saturated hydrocarbon group with 1 to 10 carbon atoms; and m is 0 or 1. The bivalent saturated hydrocarbon group may be a straight-chain alkylene group with 1 to 10 carbon atoms or branched-chain or cyclic alkylene group with 3 to 10 carbon atoms.)

Additionally, preferred examples of the tetravalent saturated hydrocarbon group expressed by general formula (4) above include the following:

[Chemical 6]

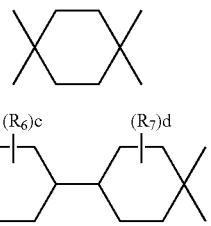

Formula

Formula

[Chemical 7]

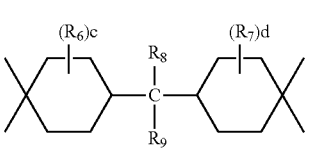

General Formula (5)

(In the formula, $R_6$, $R_7$, c and d are the same as the corresponding items in general formula (4), while $R_8$ and $R_9$ are each independently a hydrogen atom or alkyl group with 1 to 9 carbon atoms. However, the sum of carbon atoms of $R_8$ and $R_9$ is no more than 9. Additionally, the alkyl group with 1 to 9 carbon atoms may be a straight-chain alkyl group with 1 to 9 carbon atoms, branched alkyl group with 3 to 9 carbon atoms, or cyclic alkyl group with 5 to 9 carbon atoms.)

In the above formula, c and d are preferably 0, 1 or 2. Specific examples of the alkyl group with 1 to 8 carbon atoms, being represented by $R_6$ and $R_7$, are the same as those of the alkyl group represented by $R_1$, where a straight-chain or branched-chain alkyl group with 1 to 4 carbon atoms such as methyl group or the like is preferred. Also, preferably either $R_8$ or $R_9$ or both is/are each a hydrogen atom, primary alkyl group or secondary alkyl group, and if $R_8$ or $R_9$ is an alkyl group, preferably the number of carbon atoms of the alkyl group is 1 to 4.

With such saturated hydrocarbon group expressed by general formula (5), particularly preferred tetravalent saturated hydrocarbon groups include the following and the like:

[Chemical 8]

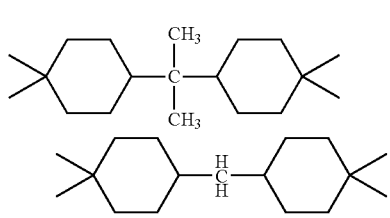

Also in general formula (1) above, X represents a hydroxyphenyl group expressed by general formula (2) below:

[Chemical 9]

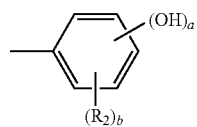

General Formula (2)

In the formula, $R_2$ is an alkyl group with 1 to 8 carbon atoms, alkoxyl group with 1 to 8 carbon atoms, aromatic hydrocarbon group, or saturated hydrocarbon group with 1 to 8 carbon atoms and having an aromatic hydrocarbon group; a is an integer of 1 to 3; and b is 0 or an integer of 1 to 4; wherein when 1≤a+b≤5 and b is 2 or greater, $R_2$s may be either the same or different. Also in general formula (2), a phenyl group that can bond with the methine group at the p-position relative to the hydroxyl group is preferred when b≤3, namely in the case of no more than three substitutions by $R_2$. Additionally when b=4, namely in the case of four substitutions by $R_2$, or when the substitution number (a) of the hydroxyl group is 1 and a substitution group is present at two m-positions relative to the hydroxyl group, then preferably the substitution position of the hydroxyl group is the o-position relative to the bonding position with the methine group from the viewpoint of facilitating synthesis.

Additionally, general formula (2) above is preferably expressed by general formula (3) below.

[Chemical 10]

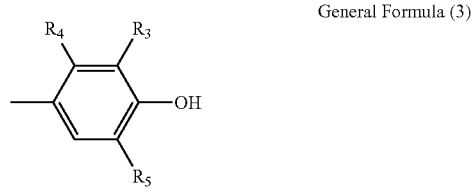

General Formula (3)

In the formula, $R_3$, $R_4$ and $R_5$ are each independently a hydrogen atom, alkyl group with 1 to 8 carbon atoms, alkoxyl group with 1 to 8 carbon atoms, aromatic hydrocarbon group, or saturated hydrocarbon group with 1 to 8 carbon atoms and having an aromatic hydrocarbon group. $R_4$ is preferably a hydrogen atom or alkyl group such as methyl group and the like.

Specific examples of the alkyl group with 1 to 8 carbon atoms or alkoxyl group with 1 to 8 carbon atoms, being represented by $R_2$, $R_3$, $R_4$ or $R_5$, are the same as those of the alkyl group or alkoxyl group represented by $R_1$, where a straight-chain or branched-chain alkyl group or alkoxyl group, with 1 to 4 carbon atoms, or cyclic alkyl group or cyclic alkoxyl group with 5 to 8 carbon atoms is preferred, but a straight-chain or branched-chain alkyl group with 1 to 4 carbon atoms is more preferred, and the methyl group is particularly preferred.

In addition, specific examples of the aromatic hydrocarbon group or saturated hydrocarbon group with 1 to 8 carbon atoms and having an aromatic hydrocarbon group, being represented by $R_2$, $R_3$, $R_4$ or $R_5$, are the same as those of the aromatic hydrocarbon group or saturated hydrocarbon group having an aromatic hydrocarbon group represented by $R_1$, where the aromatic hydrocarbon group may or may not be substituted with alkyl group and/or alkoxyl group such as methyl group, methoxy group or the like and specific examples include the phenyl group and 4-methylphenyl group etc., where the total number of carbon atoms of the substituted alkyl group is preferably 1 to 4.

With the hydroxyphenyl group in general formula (2) or (3), the substitution number of the aromatic hydrocarbon group is preferably 0 or 1, while the substitution position of the aromatic hydrocarbon group is preferably the o-position of the hydroxyl group.

Accordingly, specific examples of the substitution phenyl group expressed by general formula (2) or (3) above where there is one hydroxyl group (a=1) include, for example, 4-hydroxyphenyl group, 3-methyl-4-hydroxyphenyl group, 2-methyl-4-hydroxyphenyl group, 2,5-dimethyl-4-hydroxyphenyl group, 3,5-dimethyl-4-hydroxyphenyl group, 2,3,5-trimethyl-4-hydroxyphenyl group, 3-ethyl-4-hydroxyphenyl group, 3-isopropyl-4-hydroxyphenyl group, 3-t-butyl-4-hydroxyphenyl group, 3-t-butyl-6-methyl-4-hydroxyphenyl group, 3,5-di-t-butyl-4-hydroxyphenyl group, 3-sec-butyl-4-hydroxyphenyl group, 3-t-octyl-4-hydroxyphenyl group, 3-t-butyl-5-methyl-4-hydroxyphenyl group, 2-cyclohexyl-4-hydroxyphenyl group, 3-cyclohexyl-4-hydroxyphenyl group, 2-cyclohexyl-5-methyl-4-hydroxyphenyl group, 2-methyl-5-cyclohexyl-4-hydroxyphenyl group, 3-cyclopentyl-4-hydroxyphenyl group, 5-methyl-2-hydroxyphenyl group, 4,6-dimethyl-2-hydroxyphenyl group, 3,4,6-trimethyl-2-hydroxyphenyl group, 3,5-di-t-butyl-2-hydroxyphenyl group, 5-t-octyl-2-hydroxyphenyl group, 3-methoxy-4-hydroxyphenyl group, 3-n-hexyloxy-4-hydroxyphenyl group, 3-n-octyloxy-4-hydroxyphenyl group, 5-butoxy-2-hydroxyphenyl group, 3-phenyl-4-hydroxyphenyl group, 5-methyl-3-phenyl-4-hydroxyphenyl group, 3-(4-methylphenyl)-4-hydroxyphenyl group, 5-phenyl-2-hydroxyphenyl group, 5-(α-cumyl)-2-hydroxyphenyl group, 3-(1-phenylethyl)-4-hydroxyphenyl group, 3-benzyl-4-hydroxyphenyl group, and 3-(4-methylphenyl) methyl-4-hydroxyphenyl group, etc.

The material phenols corresponding to the above are phenols with a substitution number (b) of maximum 4, where when b=4, preferably the o-position of the hydroxyl group is not substituted. Preferred phenols are those whose p-position is not substituted and whose substitution group number (b) is no more than 3, where phenols corresponding to general formula (3) are particularly preferred.

Specific examples of the substitution phenyl group expressed by general formula (2) or (3) above, where there are two or three hydroxyl groups (a=2 or 3), include 2,4-dihydroxyphenyl group, 3,4-dihydroxyphenyl group, 2,5-dihydroxyphenyl group, 2-methyl-4,5-dihydroxyphenyl group, 3-methyl-4,5-dihydroxyphenyl group, 5-methyl-2,4-dihydroxyphenyl group, and 2,3,4-trihydroxyphenyl group, etc.

Accordingly, specific examples of the polynuclear poly (phenol) expressed by general formula (1) include, for example:

2,2-bis[4,4-bis{3-bis(2,5-dimethyl-4-hydroxyphenyl)methyl-4-hydroxy-5-methylphenyl}cyclohexyl]propane;

[Chemical 11]

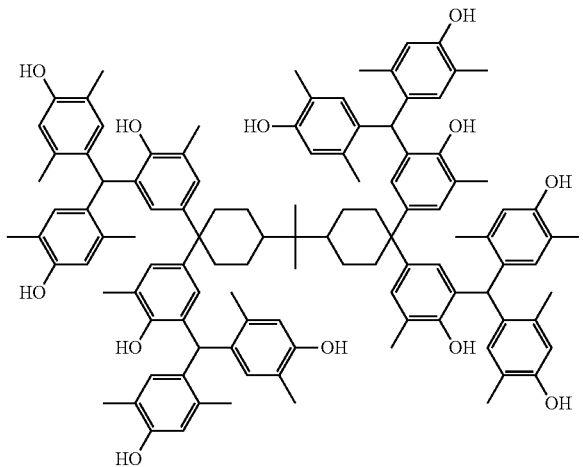

and further, 1,1,4,4-tetrakis{3-bis(2,5-dimethyl-4-hydroxyphenyl)methyl-4-hydroxy-5-methylphenyl}cyclohexane, 4,4,4',4'-tetrakis{3-bis(2,5-dimethyl-4-hydroxyphenyl)methyl-4-hydroxy-5-methylphenyl}-1,1'-bicyclohexane, bis[4,4-bis{3-bis(2,5-dimethyl-4-hydroxyphenyl)methyl-4-hydroxy-5-methylphenyl}cyclohexyl]methane, 1,1,2,2-tetrakis{3-bis(2,5-dimethyl-4-hydroxyphenyl)methyl-4-hydroxy-5-methylphenyl}ethane, and 2,2-bis[4,4-bis{3-bis(4,5-dihydroxy-2-methylphenyl)methyl-4-hydroxy-5-methylphenyl}cyclohexyl]propane; and further 2,2-bis[4,4-bis{3-bis(5-cyclohexyl-4-hydroxy-2-methylphenyl)methyl-4-hydroxy-5-methylphenyl}cyclohexyl]propane, 2,2-bis[4,4-bis{3-bis(4-hydroxy-3-methylphenyl)methyl-4-hydroxy-5-methylphenyl}cyclohexyl]propane, 2,2-bis[4,4-bis{3-bis(3,5-dimethyl-4-hydroxyphenyl)methyl-4-hydroxy-5-methylphenyl}cyclohexyl]propane, 2,2-bis[4,4-bis{3-bis(4-hydroxy-3-isopropylphenyl)methyl-4-hydroxy-5-methyl phenyl}cyclohexyl]propane, and 2,2-bis[4,4-bis{3-bis(2,3,5-trimethyl-4-hydroxyphenyl)methyl-4-hydroxy-5-methylphenyl}cyclohexyl]propane, etc.

The method for manufacturing such a novel polynuclear poly(phenol) family expressed by general formula (1) above is not specifically limited, but it can be manufactured, for example, using a method similar to the one described in WO2007/142353.

To be specific, it can be manufactured by causing a tetrakis(formylphenol) family expressed by general formula (6) below to react with phenols expressed by general formula (7) below in the presence of an acid catalyst:

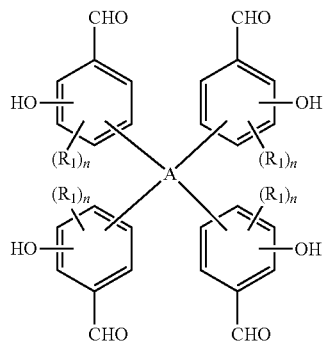

General Formula (6)

(In the formula, $R_1$, A and n are the same as the corresponding items in general formula (1).)

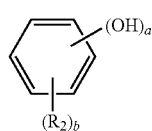

General Formula (7)

(In the formula, $R_2$, a and b are the same as the corresponding items in general formula (2).)

In general formula (6), in the formula, $R_1$, A and n are the same as the corresponding items in general formula (1), and accordingly specific, preferred examples of the tetrakis(formylphenol) family expressed by general formula (6) above include, for example:

2,2-bis{4,4-bis(3-formyl-4-hydroxy-5-methylphenyl)cyclohexyl}propane,

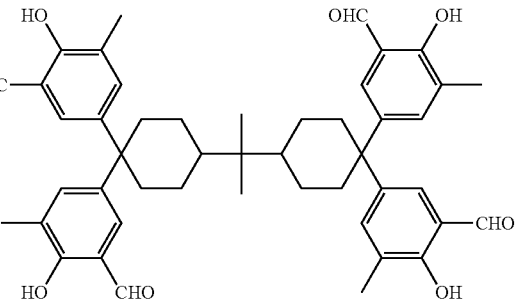

1,1,4,4-tetrakis(3-formyl-4-hydroxy-5-methylphenyl)cyclohexane, 4,4,4',4'-tetrakis(3-formyl-4-hydroxy-5-methylphenyl)-1,1'-bicyclohexane, and bis{4,4-bis(3-formyl-4-hydroxy-5-methylphenyl)cyclohexyl}methane, etc.

Such a tetrakis(formylphenol) family being the direct material expressed by general formula (6) above can be easily manufactured according to any known formylation method using a corresponding tetrakis(phenol) family as the materials. For example, to obtain 2,2-bis{4,4-bis(3-formyl-4-hydroxy-5-methylphenyl)cyclohexyl}propane as the tetrakis(formylphenol) family being the direct material, it can be easily obtained by, in an example using reaction formula (2) below, methyloling a tetrakis(methylphenol) corresponding to 2,2-bis{4,4-bis(3-formyl-4-hydroxy-5-methylphenyl)cyclohexyl}propane and then causing the obtained substance to react with a hexamethylene tetramine in the presence of acid such as trifluoroacetic acid or the like, followed by hydrolysis of the reaction product. Or, it can also be obtained according to any known Duff reaction by causing a tetrakis(methylphenol) to react with a hexamethylene tetramine in the presence of acid such as trifluoroacetic acid or the like, followed by hydrolysis of the reaction product.

Reaction Formula (2)

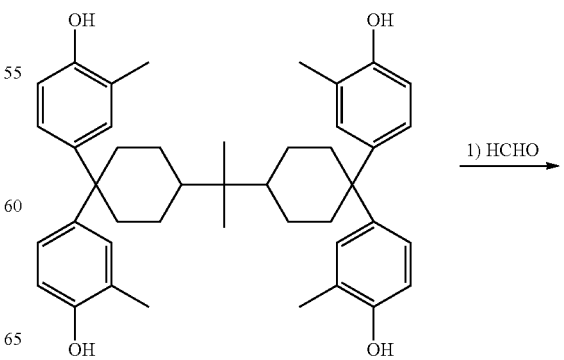

1) HCHO

-continued

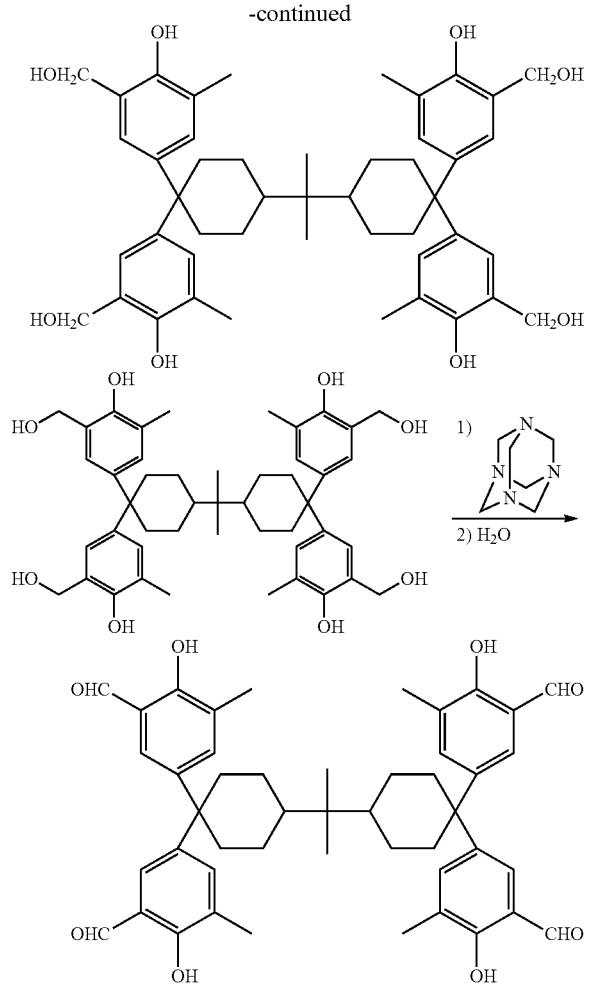

Additionally, as for the phenols expressed by general formula (7), which are the other material pertaining to the manufacture of a novel polynuclear poly(phenol) family expressed by general formula (1) above, $R_2$, a and b in the formula are the same as the corresponding items in general formula (2), and accordingly the phenols expressed by general formula (7) above are phenols at least one of whose o-position and p-position relative to the hydroxyl group is not substituted. Furthermore, preferably the substitution group number (b) is no more than 3, where phenols whose p-position and at least one of the m-positions, relative to the hydroxyl group, are not substituted are preferred from the viewpoint of facilitating synthesis, and such phenols are represented by general formula (8) below:

General Formula (8)

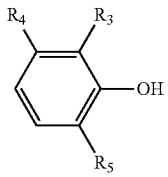

(In the formula, $R_3$, $R_4$ and $R_5$ are the same as the corresponding items in general formula (3).)

Specific examples of such phenols where there is one hydroxyl group (a=1 in general formula (7)) include, for example, phenol, 2,5-xylenol, o-cresol, p-cresol, m-cresol, 2-t-butylphenol, 2-cyclohexylphenol, 2-cyclohexyl-5-methylphenol, 2-cyclopentylphenol, 2,3,6-trimethylphenol, 2,3,5-trimethylphenol, 2-phenylphenol, 2-methyl-6-phenylphenol, and 2-methoxyphenol, etc. Furthermore, specific examples where there are two or more hydroxyl groups (a=2 or 3 in general formula (7)) include, resorcin, catechol, hydroquinone, 4-methylcatechol, 3-methylcatechol, 2-methylresorcinol, 4-methylresorcinol, and pyrogallol, etc.

For example, for 2,2-bis[4,4-bis{3-bis(2,5-dimethyl-4-hydroxyphenyl)methyl-4-hydroxy-5-methylphenyl}cyclohexyl]propane as a polynuclear poly (phenol) family, it can be obtained by, in an example using reaction formula (1) below, taking as the direct material a tetrakis(formyl-hydroxyphenyl) represented by the formula below that corresponds to the target polynuclear poly(phenol) family conforming to the present invention and then causing it to react with a phenol represented by the formula below that corresponds to the target polynuclear poly(phenol) family conforming to the present invention, in the presence of an acid catalyst.

Reaction Formula (1)

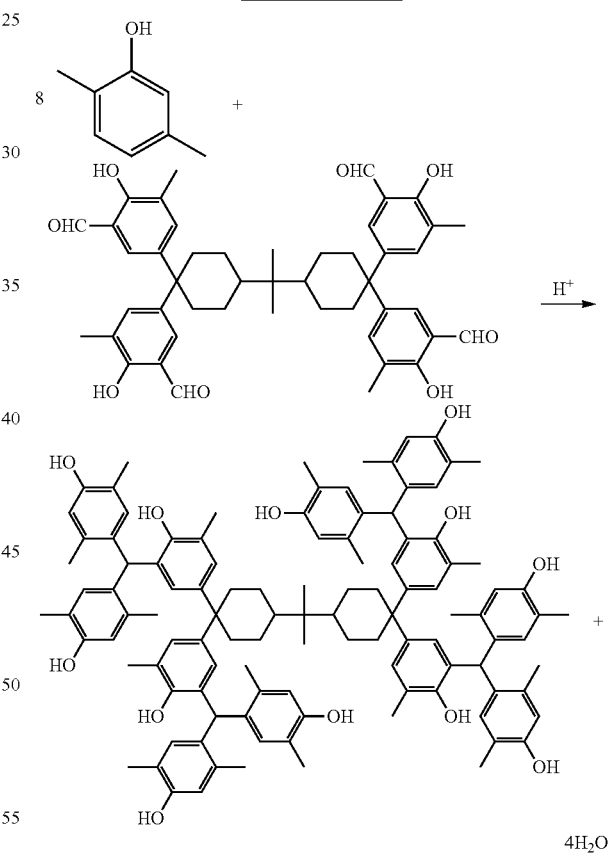

As shown in the example using reaction formula (1) above, the amount of phenols used in the reaction of the tetrakis (formyl-hydroxyphenyl) family and phenols are normally in a range of 8 to 40 mol, or preferably in a range of 9 to 20 mol, per 1 mol of tetrakis (formyl-hydroxyphenyl), although a preferred amount used varies depending on the phenols used.

Additionally, a reaction solvent may or may not be used. However, use of a solvent is preferred when the mol ratio of phenols to tetrakis(formyl-hydroxyphenyl) family is small or the phenols have a high melting point and mixing the materials is difficult. Reaction solvents that can be used include, for example, lower aliphatic alcohols such as methanol, butanol and the like, aromatic hydrocarbons such as toluene, xylene and the like, aliphatic ketones such as methylisobutyl ketone and the like, or solvent comprising a mixture of the foregoing. Lower aliphatic alcohols are preferred, and if phenols such as catechol, resorcin or the like exhibiting a high melting point and high solubility in water are used, water can be used as a reaction solvent.

Use of such solvent is not particularly limited, but it is used normally in a range of 0.1 part by weight to 10 parts by weight, or preferably in a range of 0.5 part by weight to 5 parts by weight, relative to the phenols used.

Under the manufacturing method mentioned in the example of reaction formula (1) above, preferably the acid catalyst is one that dissolves in the reaction mixture liquid, and accordingly, an inorganic acid, or an organic acid such as organic sulfonic acid, carboxylic acid or the like, of strong acidity to medium acidity is used. Specific examples include, for example, an inorganic acid such as 35% hydrochloric acid, hydrogen chloride gas, sulfuric acid, phosphoric acid or the like, as well as an organic acid such as p-toluenesulfonic acid, methanesulfonic acid, oxalic acid or the like. The preferred amount of such acid catalyst used varies depending on the strength of the acid, etc., but it is normally used in a range of 1 percent by weight to 50 percent by weight relative to the phenols.

The reaction is implemented at temperatures normally in a range of 0° C. to 100° C., or preferably in a range of 20° C. to 60° C., in air, or more preferably in an ambience of inert gas such as nitrogen or the like, under agitation for a period normally ranging from 1 to 30 hours or so.

Under the aforementioned manufacturing method, the polynuclear phenol compound produced by the reaction can be separated and refined, if necessary, according to any known method.

Accordingly, after the end of reaction, alkali water such as an aqueous solution of sodium hydroxide or the like is added to the obtained reaction liquid to neutralize the acid, after which solvent separable from water such as toluene, xylene, methylisobutyl ketone, ether or the like is added if necessary, to separate and remove the water layer, and then the water layer is separated while the oil layer is washed with water, and, if necessary, the solvent and unreacted material phenols are distilled out of the obtained oil layer, after which a solvent is added to the remaining liquid and the liquid is crystallized or caused to precipitate and crystals or precipitates are filtered out, to obtain crystalline or non-crystalline solids. If necessary, the same crystallization or precipitation operation can be repeated once or multiple times to take out solids of higher purity.

If isolating the target polynuclear poly(phenol) compound as the reaction product by means of crystallization or precipitation as mentioned above is difficult, column separation may be used to take out and refine the reaction product, or it is also possible, in the aforementioned refining step, to remove by distillation or the like the solvent or material phenol out of the oil layer in which the compound is dissolved, to take out the reaction product as a resinous substance or resinous composition, for example.

EXAMPLES

The present invention is explained in greater detail below using examples.

Reference Example 1

Synthesis of 2,2-bis{4,4-bis(3-formyl-4-hydroxy-5-methylphenyl)cyclohexyl}propane Step 1

Synthesis of 2,2-bis{4,4-bis(4-hydroxy-3-hydroxymethyl-5-methylphenyl)cyclohexyl}propane 1020.0 g (4.08 mol) of aqueous solution of 16% sodium hydroxide was put in a four-way flask of 5 liters in capacity and the reaction container was replaced with nitrogen, after which 538.0 g (0.85 mol) of 2,2-bis{4,4-bis(4-hydroxy-5-methylphenyl)cyclohexyl}propane was added at a temperature of around 35° C., and the mixture was agitated for 1 hour. Next, 947.1 g (11.05 mol) of aqueous solution of 35% formaldehyde was added under agitation over a period of 2 hours at 25 to 30° C. to cause reaction. Thereafter, the mixture was agitated at 30° C. for 5 hours to cause reaction.

After the reaction had ended, the mixture was cooled to 10° C. and 550.8 g of methylethyl ketone was dripped over a period of 20 minutes, after which 1280.0 g of methylisobutyl ketone was added. Thereafter, 661.8 g of aqueous solution of 17.5% hydrochloric acid was added to neutralize the liquid, which was then heated to 30° C. and let stand for 10 minutes to remove the water layer. Thereafter, 640.0 g of water was added and the mixture was agitated, followed by removing the water layer. From the obtained oil layer, 1021.5 g of solvent was distilled out at 45° C. under decompression, after which 1280.0 g of toluene was added and the mixture was cooled to precipitate crystals. The precipitated crystals were filtered out to obtain 870.2 g of crude crystals.

Thereafter, these obtained crude crystals, 960.0 g of methylethyl ketone, 1700.0 g of methylisobutyl ketone and 800 g of water were put in a four-way flask of 5 liters in capacity, and the mixture was heated to 45° C. to dissolve the crystals and then let stand to remove the water layer, after which 1470.5 g of solvent was distilled out from the obtained oil layer at 45° C. under decompression (crystals precipitated in the middle) and the remaining liquid was cooled to 20° C., after which it was filtered and dried to obtain 224.8 g of target white powder (purity as measured by high-speed liquid chromatography was 93.3%). The white powder was confirmed by proton NMR analysis to be the target compound. The yield relative to the material tetrakisphenol was 35.1%.

TABLE 1

1H-NMR (400 MHz) identification results
(internal reference: tetramethylsilane)

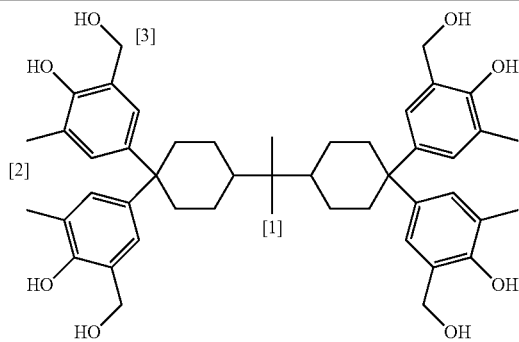

1H-NMR measurement (400 MHz/solvent: DMSO-d6)

TABLE 1-continued

1H-NMR (400 MHz) identification results
(internal reference: tetramethylsilane)

| Shift value (ppm) | Number of protons | Signal | Assignment |
|---|---|---|---|
| 0.46 | 6 | s | —CH$_3$ [1] |
| 1.05-1.14 | 4 | m | —CH$_2$ (cyclohexyl) |
| 1.30-1.36 | 2 | m | —CH (cyclohexyl) |
| 1.51-1.54 | 4 | m | —CH$_2$ (cyclohexyl) |
| 1.63-1.69 | 4 | m | —CH$_2$ (cyclohexyl) |
| 2.05-2.12 | 12 | m | —CH$_3$ [2] |
| 2.66-2.69 | 4 | m | —CH$_2$ (cyclohexyl) |
| 4.45-4.53 | 8 | m | —CH$_2$ [3] |
| 5.21-5.27 | 4 | m | —OH |
| 6.76-7.03 | 8 | m | Ph—H |
| 8.11-8.15 | 4 | m | Ph—OH |

Step 2

Synthesis of 2,2-bis{4,4-bis(3-formyl-4-hydroxy-5-methylphenyl)cyclohexyl}propane 461.7 g (4.05 mol) of trifluoroacetic acid was put in a four-way flask of 3 liters in capacity and the reaction container was replaced with nitrogen, after which 83.3 g (0.594 mol) of hexamethylenetetramine was added at a temperature of around 30° C., and 101.7 g (0.135 mol) of 2,2-bis{4,4-bis(4-hydroxy-3-hydroxymethyl-5-methylphenyl)cyclohexyl}propane(methylol) obtained in step 1 was added under agitation over a period of 1 hour and 30 minutes at 60° C. to cause reaction. Thereafter, the mixture was agitated further at 80° C. for 16 hours to cause reaction.

251.5 g of water was added to the liquid obtained after the end of reaction and the mixture was hydrolyzed at 60° C. for 1 hour. During the course of hydrolysis, viscous solids precipitated. 201.2 g of toluene and 301.8 g of methylisobutyl ketone were added to the resulting mixture liquid and the mixture was heated to 70° C. to dissolve the solids and then let stand to remove the water layer. Thereafter, 444.8 g of aqueous solution of 16% sodium hydroxide was added to neutralize the liquid, which was then cooled, where crystals precipitated during cooling. The liquid was cooled to 20° C. and then precipitates were filtered out to obtain 104.0 g of crude crystals.

Thereafter, these obtained crude crystals and 1814.0 g of tetrahydrofuran were put in a four-way flask of 3 liters in capacity, and the mixture was heated to 60° C. to dissolve the crystals and then 1449.0 g of solvent was distilled out at normal pressure. Crystals precipitated in the middle. 240.0 g of water and 144.0 g of acetone were added to the remaining liquid and the mixture was cooled to 20° C., after which it was filtered and dried to obtain 71.2 g of target yellow powder (purity as measured by high-speed liquid chromatography was 96.2%). The yellow powder was confirmed by proton NMR analysis to be the target compound. The yield relative to the material methylol was 70.8%.

TABLE 2

1H-NMR (400 MHz) identification results
(internal reference: tetramethylsilane)

[Structural formula of 2,2-bis{4,4-bis(3-formyl-4-hydroxy-5-methylphenyl)cyclohexyl}propane with labels [1] and [2]]

1H-NMR measurement (400 MHz/solvent: DMSO-d6)

| Shift value (ppm) | Number of protons | Signal | Assignment |
|---|---|---|---|
| 0.47 | 6 | s | —CH$_3$ [1] |
| 1.05-1.14 | 4 | m | —CH$_2$ (cyclohexyl) |
| 1.38-1.43 | 2 | m | —CH (cyclohexyl) |
| 1.59-1.62 | 4 | m | —CH$_2$ (cyclohexyl) |
| 1.74-1.77 | 4 | m | —CH$_2$ (cyclohexyl) |
| 2.10-2.18 | 12 | m | —CH$_3$ [2] |
| 2.79-2.82 | 4 | m | —CH$_2$ (cyclohexyl) |
| 7.34-7.69 | 8 | m | Ph—H |
| 9.97-10.06 | 4 | m | Ph—OH |
| 10.83-10.91 | 4 | m | —CHO |

Example 1

Synthesis of 2,2-bis[4,4-bis{3-bis(2,5-dimethyl-4-hydroxyphenyl)methyl-4-hydroxy-5-methylphenyl}cyclohexyl]propane 48.8 g (0.4 mol) of 2,5-xylenol and 48.8 g of methanol were put in a four-way flask of 1 liter in capacity and the reaction container was replaced with nitrogen, after which 24.7 g of hydrochloric acid gas was blown in at 30° C. Thereafter, a solution prepared by dissolving 48.8 g (0.4 mol) of 2,5-xylenol in 97.6 g of methanol was dripped, and then 59.6 g (0.08 mol) of 2,2-bis[4,4-bis(3-formyl-4-hydroxy-5-methylphenyl)cyclohexyl]propane was added under agitation over a period of 1 hour at 30° C. to cause reaction. Thereafter, the mixture was agitated further at 40° C. for 20 hours to cause reaction.

After the reaction had ended, 169.5 g of aqueous solution of 16% sodium hydroxide was added to neutralize the liquid, after which 198.0 g of methylisobutyl ketone was added and the mixture was heated to 50° C. under agitation. Next, the mixture was let stand to remove the water layer, after which 120.0 g of water was added and the mixture was agitated and washed with water and then let stand to separate the water layer. From the obtained oil layer, 130.1 g of solvent was distilled out at normal pressure, after which 130.0 g of water and 195.0 g of toluene were added and the mixture was cooled, and then solids precipitating during the course of cooling were filtered out to obtain 203.4 g of crude product. These obtained crude solids, 266.2 g of methylisobutyl ketone and 100.0 g of water were put in a four-way flask of 1 liter in capacity, and the mixture was heated to 70° C. to dissolve the solids and then let stand to remove the water layer. Thereafter, 195.3 g of solvent was distilled out at normal pressure by distillation, after which 100.0 g of water and 250.0 g of toluene were added and again 199.7 g of solvent was distilled out at normal pressure (solids precipitated during condensation). After the distillation, 60.0 g of water was added and the mixture was cooled to 25° C., after which precipitated solids were filtered out and dried to obtain 78.7 g of target light-yellow powder of 2,2-bis[4,4-bis{3-bis(2,5-dimethyl-4-hydroxyphenyl)methyl-4-hydroxy-5-methylphenyl}cyclohexyl]propane (purity as measured by high-speed liquid chromatography was 93.9%). The yield relative to the material 2,2-bis{4,4-bis(3-formyl-4-hydroxy-5-methylphenyl)cyclohexyl}propane was 59.6%.

Glass transition temperature (by differential scanning calorimetry) 196.3° C. (Melting point was not recognized.)

TABLE 3

1H-NMR (400 MHz) identification results (internal reference: tetramethylsilane)

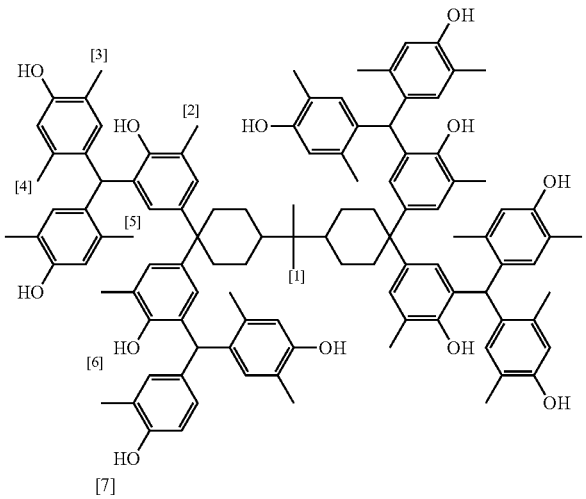

1H-NMR measurement (400 MHz/solvent: DMSO-d6)

| Shift value (ppm) | Number of protons | Signal | Assignment |
| --- | --- | --- | --- |
| 0.34 | 6 | s | —$CH_3$ [1] |
| 0.73 | 4 | s | —$CH_2$ (cyclohexyl) |
| 1.05 | 2 | s | —CH (cyclohexyl) |
| 1.19 | 4 | s | —$CH_2$ (cyclohexyl) |
| 1.41 | 4 | s | —$CH_2$ (cyclohexyl) |
| 1.83-2.09 | 64 | m | —$CH_2$ (cyclohexyl) + —$CH_3$ ([2] + [3] + [4]) |
| 5.65-5.71 | 4 | m | —CH [5] |
| 6.30-6.62 | 24 | m | Ph—H |
| 7.73-7.82 | 4 | m | Ph—OH [6] |
| 8.77 | 8 | s | Ph—OH [7] |

What is claimed is:

1. A polynuclear poly(phenol) family expressed by general formula (1) below:

[Chemical 1]

General Formula (1)

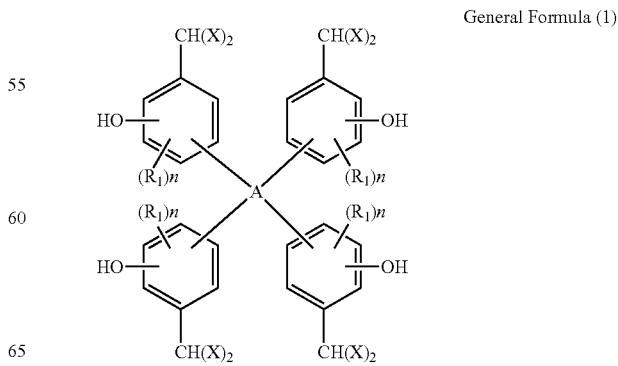

(in the formula, $R_1$s are each independently an alkyl group with 1 to 8 carbon atoms, alkoxyl group with 1 to 8 carbon atoms, aromatic hydrocarbon group, or saturated hydrocarbon group with 1 to 8 carbon atoms and having an aromatic hydrocarbon group; n is 0 or an integer of 1 to 3; X is a hydroxyphenyl group expressed by general formula (2) below; and A is a tetravalent carbon atom group or tetravalent saturated hydrocarbon group with 2 or more carbon atoms; wherein when A is a tetravalent saturated hydrocarbon group with 2 or more carbon atoms, two carbon atoms in the A group are each bonded to two phenyl groups);

[Chemical 2]

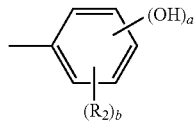

General Formula (2)

(in the formula, $R_2$ is an alkyl group with 1 to 8 carbon atoms, alkoxyl group with 1 to 8 carbon atoms, aromatic hydrocarbon group, or saturated hydrocarbon group with 1 to 8 carbon atoms and having an aromatic hydrocarbon group; a is an integer of 1 to 3; and b is 0 or an integer of 1 to 4; wherein when $1 \le a+b \le 5$ and b is 2 or greater, $R_2$s may be either the same or different).

2. A polynuclear poly(phenol) family according to claim 1, wherein general formula (2) above is expressed by general formula (3) below:

[Chemical 3]

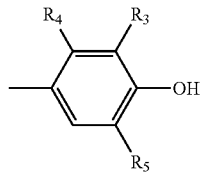

General Formula (3)

(in the formula, $R_3$, $R_4$ and $R_5$ are each independently a hydrogen atom, alkyl group with 1 to 8 carbon atoms, alkoxyl group with 1 to 8 carbon atoms, aromatic hydrocarbon group, or saturated hydrocarbon group with 1 to 8 carbon atoms and having an aromatic hydrocarbon group).

* * * * *